US011039821B2

(12) United States Patent
Sawada et al.

(10) Patent No.: US 11,039,821 B2
(45) Date of Patent: Jun. 22, 2021

(54) DRUG SUPPLY DEVICE

(71) Applicant: TERUMO KABUSHIKI KAISHA, Tokyo (JP)

(72) Inventors: Satoshi Sawada, Kanagawa (JP); Hideaki Shibata, Kanagawa (JP); Naoki Ishii, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 149 days.

(21) Appl. No.: 16/126,453

(22) Filed: Sep. 10, 2018

(65) Prior Publication Data

US 2019/0000434 A1   Jan. 3, 2019

Related U.S. Application Data

(63) Continuation of application No. PCT/JP2017/009664, filed on Mar. 10, 2017.

(30) Foreign Application Priority Data

Mar. 11, 2016   (JP) .............................. JP2016-047970

(51) Int. Cl.
*A61B 17/00* (2006.01)
*A61M 37/00* (2006.01)
*A61K 9/70* (2006.01)

(52) U.S. Cl.
CPC .......... *A61B 17/00234* (2013.01); *A61K 9/70* (2013.01); *A61M 37/00* (2013.01);
(Continued)

(58) Field of Classification Search
CPC .. A61M 2025/1004; A61M 2025/0057; A61M 37/00; A61M 25/0074; A61K 9/70; A61B 17/00234; A61B 5/6858
See application file for complete search history.

(56) References Cited

U.S. PATENT DOCUMENTS 6,893,431 B2   5/2005   Naimark et al.
7,976,496 B2   7/2011   Kennedy, II et al.
(Continued)

FOREIGN PATENT DOCUMENTS

| JP | 2003521326 A | 7/2003 |
| JP | 2005506122 A | 3/2005 |
| WO | 2016005946 A2 | 1/2016 |

OTHER PUBLICATIONS

International Search Report (PCT/ISA/210) dated May 23, 2017, by the Japanese Patent Office as the International Searching Authority for International Application No. PCT/JP2017/009664.
(Continued)

*Primary Examiner* — Bhisma Mehta
*Assistant Examiner* — Hamza A Darb
(74) *Attorney, Agent, or Firm* — Buchanan Ingersoll & Rooney PC

(57) ABSTRACT

A drug supply device for supplying drug to a living body surface that includes a shaft and a drug holding sheet attached to the distal end of the shaft. The drug holding sheet has a first face that faces distally and a second face opposite the first face that faces proximally when the drug holding sheet is expanded. The drug holding sheet includes folded portions that fold such that the first face is positioned to face radially inward while exposing the second face to an outside environment when the drug holding sheet is in a folded state. A drug is applied on the first face of the drug holding sheet. The drug supply device includes an expandable member on the second face of the drug holding sheet. The expandable member is expandable to cause the drug holding sheet to expand from the folded state into the expanded state.

20 Claims, 6 Drawing Sheets

(52) U.S. Cl.
CPC ............... *A61B 2017/00623* (2013.01); *A61B 2017/00659* (2013.01)

(56) References Cited

U.S. PATENT DOCUMENTS

| | | | |
|---|---|---|---|
| 10,195,366 B1* | 2/2019 | Kiani | A61M 5/422 |
| 2003/0073979 A1 | 4/2003 | Naimark et al. | |
| 2004/0215231 A1* | 10/2004 | Fortune | A61B 17/11 606/213 |
| 2007/0119461 A1* | 5/2007 | Biancucci | A61B 17/12122 128/846 |
| 2014/0296798 A1* | 10/2014 | Venkatraman | A61L 31/16 604/285 |
| 2015/0119851 A1* | 4/2015 | Hoogenakker | A61B 17/00234 604/507 |

OTHER PUBLICATIONS

Written Opinion (PCT/ISA/237) dated May 23, 2017, by the Japanese Patent Office as the International Searching Authority for International Application No. PCT/JP2017/009664.

The extended European Search Report dated Nov. 11, 2019, by the European Patent Office in corresponding European Patent Application No. 17763420.1-1132. (6 pages).

An English Translation of the International Search Report (Form PCT/ISA/210) and the Written Opinion of the International Searching Authority (Form PCT/ISA/237) dated May 23, 2017, by the Japanese Patent Office in corresponding International Application No. PCT/JP2017/009664. (7 pages).

* cited by examiner

DRUG SUPPLY DEVICE

CROSS-REFERENCES TO RELATED APPLICATIONS

This application is a continuation of International Application No. PCT/JP2017/009664 filed on Mar. 10, 2017, and claims priority to Japanese Patent Application No. 2016-047970 filed on Mar. 11, 2016, the entire content of both of which is incorporated herein by reference.

TECHNICAL FIELD

The present invention generally relates to a drug supply device, and particularly to a medical device for supplying a drug to a surface of a living body.

BACKGROUND ART

When a lesion affected area occurs in the body of a patient, a treatment involving inserting a catheter or the like into the body and administrating a drug to the lesion affected area has been known.

For example, U.S. Pat. No. 6,893,431 discloses a medical device in which an expandable structure body is attached to a distal portion of a catheter and a therapeutic patch (to which drug is fixed) is disposed on the expandable structure body such that, after the catheter is inserted into the body, the structure body is expanded to attach the therapeutic patch to the lesion affected area. The structure body is configured from a plurality of wire parts expandable to an umbrella shape and the therapeutic patch is disposed on the plurality of wire parts such that the therapeutic patch is expanded by expanding the plurality of wire parts. Then, the expanded therapeutic patch is brought into contact with a living body surface such as the outer side face, the inner side face or the like of an organ in the body to supply the drug to the living body surface.

SUMMARY OF INVENTION

Treatment that suppresses the invasiveness to the living body can be achieved without performing an extensive surgery by delivering a therapeutic patch to a lesion affected area through a catheter in the manner described above.

However, the medical device disclosed in U.S. Pat. No. 6,893,431 has a problem in that the structure of the expandable structure body that can expand the plurality of wire parts to an umbrella shape is complicated.

Further, when the plurality of wire parts are folded in such a manner as to close the umbrella, the therapeutic patch disposed on the plurality of wire parts is also folded. The therapeutic patch is inserted into the body of a patient in this state (i.e., with the therapeutic patch also folded). Although the therapeutic patch is in a folded state, however, the surface of the therapeutic patch to which drug is fixed is exposed to the outer side (i.e., the surface with the drug is exposed to the environment in the living body). Therefore, there is the possibility that the surface of the therapeutic patch may be brought into contact with some location of the medical device or a component within the body of the patient when the therapeutic patch is moved to the living body surface. This unintended contact can make appropriately supplying the drug to the targeted living body surface relatively more difficult.

The drug supply device and drug supply method disclosed here can supply a drug to the living body surface with (increased) certainty while the drug supply device maintains a (relatively) simple structure.

A drug supply device is disclosed for supplying drug to a living body surface. The drug supply device including an elongate shaft, a drug holding sheet attached to a distal end of the shaft and having a first face that is directed to a front of the shaft when the drug holding sheet is expanded (developed) and has drug held thereon and a second face that is directed to a proximal side of the shaft. The drug holding sheet further having a plurality of folded portions capable of being folded such that the first face is positioned on an inner side, and an expandable member disposed on the second face of the drug holding sheet that is expandable and contractible to expand and contract the plurality of folded portions of the drug holding sheet. The drug supply device supplies the drug held on the first face of the drug holding sheet in a state in which the development member is deformed to develop the plurality of folded portions into the expanded state.

Preferably, the drug holding sheet forms a quadrangle centered at a portion thereof attached to the distal of the shaft when the drug holding sheet is developed, the plurality of folded portions includes four first folded portions of a triangular shape folded such that four corners of the drug holding sheet overlap with the center of the quadrangle and four second folded portions folded such that straight line portions positioned between adjacent ones of the first folded portions form mountain portions that project toward the front of the shaft and straight line portions that pass the center of the quadrangle and bisect the individual first folded portions form valley portions that project toward the proximal side of the shaft, and the development member is disposed along two diagonals of the quadrangle.

In this case, when the drug holding sheet is developed by the development member, after the four second folded portions are individually developed, preferably the four first folded portions are individually developed.

Preferably, the drug holding sheet is attached to the distal of the shaft such that, when the plurality of folded portions is developed, the first face extends substantially perpendicularly to the shaft.

The development member may be configured from a plurality of balloons in which development fluid can circulate. Preferably, each of the plurality of balloons has a plurality of bendable nodes, and when the development fluid is injected, the plurality of balloons are extended substantially perpendicularly to the shaft, but when the development fluid is sucked, the plurality of balloons are gradually curved at multiple stages so as to become concave toward the front of the shaft.

Further, the development member may be configured from a shape memory member.

At a distal portion of the development member disposed along the two diagonals of the quadrangle, a needle-shaped member may be disposed which projects toward the front of the shaft when the drug holding sheet is developed. In this case, the drug supply device further includes a patch-shaped therapeutic held on the needle-shaped member. Furthermore, the drug supply device may be configured such that the needle-shaped member is removably disposed on the development member and is indwelled on a living body surface together with the patch-shaped therapeutic.

The drug supply device may be configured such that it further includes a patch-shaped therapeutic adhered to the first face of the drug holding sheet by temperature-response bonding agent, and, when a given temperature is exceeded, the patch-shaped therapeutic is removed from the first face of the drug holding sheet and is indwelled on the living body surface.

Further, the drug supply device may be configured such that the development member disposed along the two diagonals of the quadrangle has a drug supply lumen, and drug supplied through the drug supply lumen is discharged from a distal portion of the development member.

Further, preferably the shaft has a lumen formed along an axial direction of the shaft.

Another aspect of the disclosure involves a drug supply device for supplying a drug to a surface of a treatment site within a living body. The drug supply device includes an elongated shaft extending in an axial direction and a drug holding sheet attached to the distal end of the shaft. The drug holding sheet includes a first surface and a second surface opposite the first surface. The first surface of the drug holding sheet is coated with a drug. The drug holding sheet includes a fold pattern of fold lines that causes the drug holding sheet to be planar when the drug holding sheet is fully unfolded in an unfolded state and causes the drug holding sheet to be folded when the drug holding sheet is fully folded into a folded state. The drug holding sheet has an interior when folded into the folded state. An expandable member is connected to the second face of the drug holding sheet. The expandable member is expandable to expand the drug holding sheet from the folded state into the unfolded state. The first surface of the drug holding sheet faces distally from the distal end of the elongated shaft when the drug holding sheet is in the unfolded state and the second surface of the drug holding sheet faces proximally towards the proximal end of the elongated shaft when the drug holding sheet is in the unfolded state. The first surface of the drug holding sheet faces inward when the drug holding sheet is in the folded state and the second surface of the drug holding sheet faces outward when the drug holding sheet is in the folded state such that the second surface directly faces an environment beyond the drug supply device while portions of the first surface face one another by facing towards the interior. The drug supply device is configured to supply the drug on the first face of the drug holding sheet to the surface of the treatment site in the living body by contacting the surface of the treatment site in the living body when the expandable member is expanded to cause the drug holding sheet to expand into the expanded state.

Yet another aspect of the disclosure involves a method that includes moving a drug supply device within a living body, the drug supply device including a drug holding sheet which has a first side and a second side opposite the first side, the first side of the drug holding sheet being coated with a drug, the drug holding sheet being folded throughout the moving of the drug supply device within the living body so that the first side of the drug holding sheet is not exposed to the living body. The method includes positioning the drug holding sheet of the drug supply device at a treatment site within the living body and unfolding the drug holding sheet when the drug holding sheet is positioned at the treatment site within the living body. The unfolding of the drug holding sheet causes the first side of the drug holding sheet to directly face the treatment site. The method includes applying the drug on the drug holding sheet to the treatment site within the living body by contacting the treatment site with the drug holding sheet.

The disclosed drug supply device can supply the drug with certainty to the living body surface while possessing a relatively simple structure because the drug supply device includes the drug holding sheet having the plurality of first folded portions individually folded such that the first face on which the drug is held is positioned on the inner side and the drug supply device includes the expandable member disposed on the second face of the drug holding sheet and deformable to develop the plurality of folded portions.

14 when the drug holding sheet is developed so as to extend along the living body surface.

Figure 17:
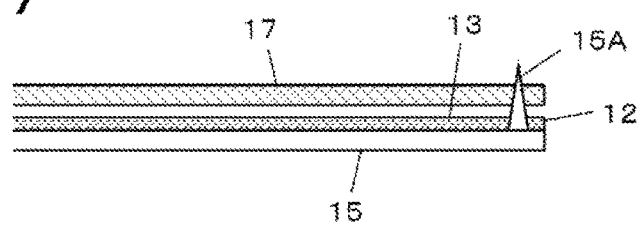

FIG. 17 is a partial sectional view depicting a drug supply device according to another embodiment when a drug holding sheet is developed.

Figure 18:
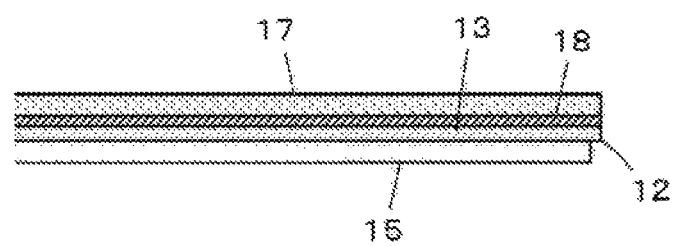

FIG. 18 is a partial sectional view depicting a drug supply device according to another embodiment when a drug holding sheet is developed.

Figure 19:
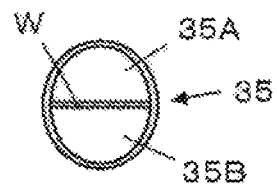

FIG. 19 is a sectional view depicting a balloon used in a drug supply device of another embodiment.

MODES FOR CARRYING OUT THE INVENTION

Set forth below is a detailed description of embodiments of a drug supply device and drug supply method representing examples of the inventive drug supply device and method disclosed here. Note that, for the convenience of description, there are cases where the dimensional ratios of the drawings are exaggerated and are different from the actual ratios.

Embodiment 1

Figure 1:
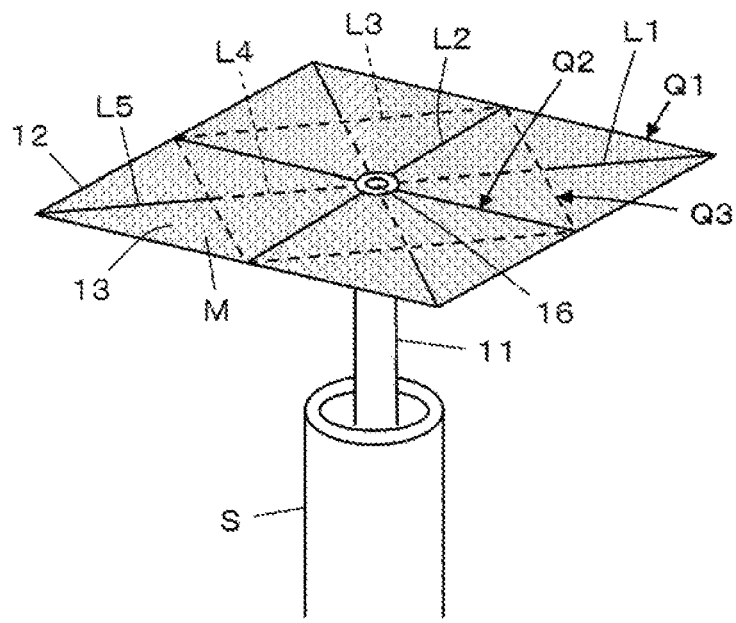
FIG. 1 is a front side perspective view of a drug supply device according to an embodiment as viewed from the front of a shaft when a drug holding sheet is expanded.
Figure 2:
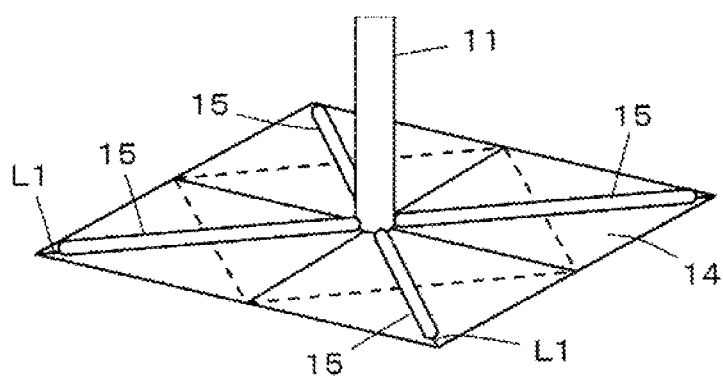
FIG. 2 is a rear side perspective view of the drug supply device according to the embodiment as viewed from the proximal side of the shaft when the drug holding sheet is expanded.

FIGS. 1 and 2 depict configurations of one embodiment of the disclosed drug supply device. The drug supply device includes an elongate shaft 11 and a developable (i.e., expandable and contractible) drug holding sheet 12 disposed at the distal end of the shaft 11. FIG. 1 is a perspective view of the drug supply device, in which the drug holding sheet 12 is developed to a planar state (i.e., expanded so that the drug holding sheet 12 forms a plane, i.e., is planar) as viewed from the front (i.e., viewed from beyond the distal end, looking proximally) of the shaft 11. FIG. 2 is a perspective view of the drug supply device, in which the drug holding sheet 12 is expanded to a planar state, as viewed from the proximal side of the shaft 11 (i.e., viewed from proximal to the drug holding sheet 12, looking distally).

The drug holding sheet 12 is attached to an outer periphery of the distal end of the shaft 11 such that, when it is expanded, the drug holding sheet 12 forms a square (quadrangle) Q1 centered at a portion thereof at which it is attached to the distal end of the shaft 11 (i.e., the drug holding sheet 12 is attached to the distal end of the shaft 11 at the center of the drug holding sheet 12). The drug holding sheet 12 extends substantially perpendicularly to the shaft 11 when it is expanded.

The drug holding sheet 12 has a first face 13 (a first surface) directed toward the front of the shaft 11 (i.e., facing distally) when the drug holding sheet 12 is expanded as depicted in FIG. 1, and a second face 14 (second surface) directed toward the proximal side of the shaft 11 (i.e., facing proximally) when the drug holding sheet 12 is expanded as depicted in FIG. 2. Drug M is held on the overall area of the first face 13 (i.e., the drug M coats or is applied on the first surface of the drug holding sheet 12). Four balloons 15 are disposed on the second face 14. The four balloons 15 are deformable to a bar-like shape (i.e., an elongated linear shape) by being individually expanded along two diagonals L1 of the square Q1 of the drug holding sheet 12 centered at the shaft 11.

Figure 3:
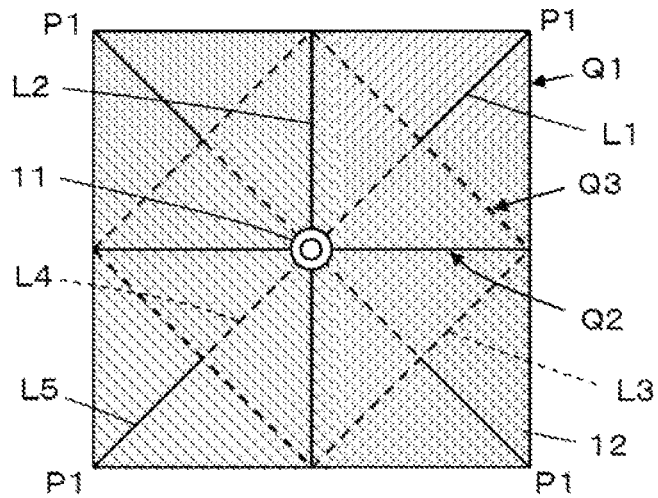
FIG. 3 is a front elevational view of the expanded drug holding sheet in the embodiment as viewed from the front of the shaft.

The drug holding sheet 12 has a fold pattern along a plurality of fold lines in advance (i.e., the drug holding sheet 12 is configured to fold in a particular manner, in accordance with a predetermined fold pattern). The plurality of fold lines includes:

(1) two straight lines L2 extending along the sides of the square Q1 (i.e., parallel to the side edges of the square Q1) and passing through the center of the square Q1, (2) four diagonals L3 that are diagonal lines of four squares Q2 into which the square Q1 is divided by the two straight lines L2 and which do not overlap with the diagonals L1 of the square Q1 (i.e., the diagonals of the square Q1 are defined by the diagonal L1 toward the outer periphery and the diagonal L4 that is toward the center as shown in FIG. 3), (3) two straight lines L4 that overlap with the two diagonals L1 of the square Q1 and are positioned on the inner side of a square Q3 formed from the four diagonals L3, and (4) four straight lines L5 that overlap with the two diagonals L1 of the square Q1 and are positioned on the outer side of the square Q3 formed from the four diagonals L3.

The fold lines described above and shown in FIGS. 1-3 have such a fold habit (i.e., predisposition to fold or a fold pattern) that the two straight lines L2 and the four straight lines L5 indicated by solid lines in FIGS. 1 and 3 form mountain portions that project toward the front of the shaft 11 (i.e., distally) and the four diagonals L3 and the straight lines L4 indicated by broken lines form valley portions that project toward the proximal side of the shaft 11 (i.e., proximally).

The shaft 11 has a lumen 16 formed along an axial direction of the shaft 11. The lumen 16 is configured such that an endoscope for universal use or an image diagnosis device such as an intravascular ultrasonic (IVUS) or optical coherence tomography (OCT) image diagnosis device can be inserted into the lumen 16 from a proximal portion and pass through the lumen 16 to the distal end of the shaft 11 to acquire an image that captures the forward vision from the distal portion of the shaft 11 (i.e., a view looking distally beyond the distal end of the shaft 11 can be captured/imaged).

On a wall portion of the shaft 11, a balloon expansion lumen is formed which extends from the proximal portion of the shaft 11 to the disposition position of the drug holding sheet 12 at the distal portion of the shaft 11. The balloon expansion lumen communicates with the four balloons 15. The four balloons 15 configure an expansion member, such that the four balloons 15 are expanded simultaneously into a bar shape (i.e., an elongated linear shape that resembles a bar or rod) along the diagonals L1 of the square Q1 of the drug holding sheet 12 by injecting development fluid through the balloon expansion lumen. The four balloons may be contracted simultaneously by withdrawing (e.g., sucking) the expansion fluid through the balloon expansion lumen.

Although the drug holding sheet 12 has a fold pattern along the plurality of fold lines in advance as described above, if the four balloons 15 are expanded into a bar shape along the two diagonals L1 of the square Q1, then the two diagonals L1 of the square Q1 are individually extended linearly such that the drug holding sheet 12 is expanded into a flat plane as depicted in FIGS. 1 and 2.

On the other hand, if the four balloons 15 are contracted, then the force for compulsorily extending the two diagonals L1 of the square Q1 linearly is lost, and the drug holding sheet 12 is gradually folded in the following manner in accordance with the fold pattern on the fold lines.

Figure 4:
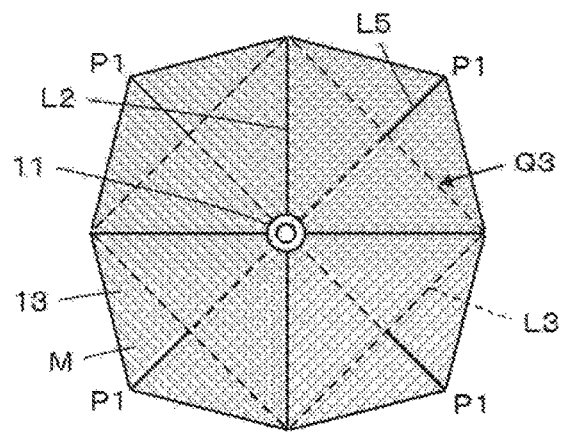
FIG. 4 is a front elevational view of the drug holding sheet as viewed from the front of the shaft, which is in an intermediate state when four first folded portions in the embodiment are folded.

That is, when the four balloons 15 are in a state in which the drug holding sheet 12 is expanded to form the square Q1 as depicted in FIG. 3 and then the four balloons 15 begin to be contracted (deflated), the drug holding sheet 12 begins to be folded at the four diagonals L3 such that the first face 13 on which the drug M is held comes to the inner side first as depicted in FIG. 4, and the four vertices P1 of the square Q1 upon development are swollen toward the front of the shaft 11.

Figure 5:
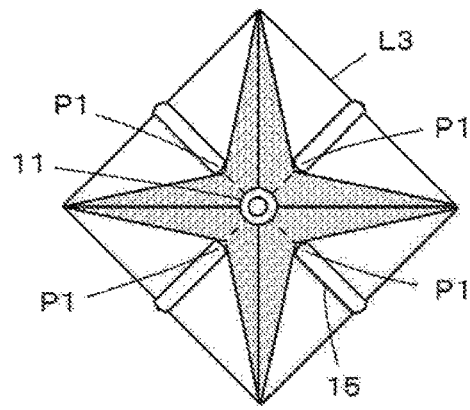
FIG. 5 is a front elevational view of the drug holding sheet as viewed from the front of the shaft, which is in another intermediate state when the four first folded portions in the embodiment are folded.
Figure 6:
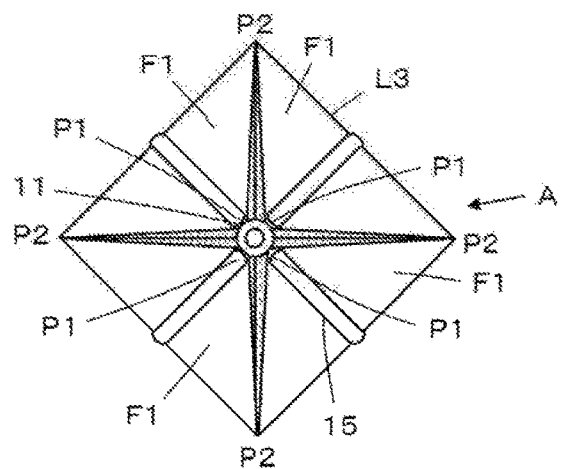
FIG. 6 is a front elevational view of the drug holding sheet as viewed from the front of the shaft, which is in a state in which the four first folded portions in the embodiment are folded.

As the folding of the drug holding sheet 12 at the four diagonals L3 proceeds, the four vertices P1 approach the distal end of the shaft 11 positioned at the center of the square Q1 as depicted in FIG. 5. The drug holding sheet 12 continues to be folded during the contraction of the four balloons 15 until the four vertices P1 are overlapped with the distal end of the shaft 11 as depicted in FIG. 6 (i.e., the four vertices P1 contract to be positioned at the distal end of the shaft 11). This folded position creates a first fold body A of a square shape in which four first folded portions F1 of a triangular shape are disposed on a plane around the distal end of the shaft 11 (i.e., the first fold body A is planar and is positioned at the distal end of the shaft 11).

Figure 7:
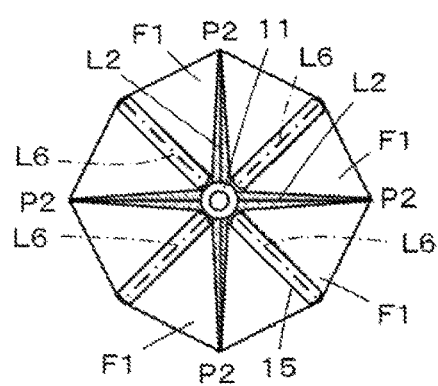
FIG. 7 is a front elevational view of the drug holding sheet as viewed from the front of the shaft, which is in an intermediate state when four second folded portions in the embodiment are folded.

If the four balloons 15 are further contracted from the fold position with the first fold body A shown in FIG. 6, the drug holding sheet 12 begins to be folded such that portions of the straight lines L2 positioned between adjacent ones of the first folded portions F1 form mountain portions projecting toward the front of the shaft 11 (i.e., protrude distally) and portions of straight lines L6 that bisect the first folded portions F1 form valley portions (i.e., contract proximally) as depicted in FIG. 7, and the four vertices P2 of the first fold body A move toward the front of the shaft 11 (i.e., contract inward toward the center of the drug holding sheet 12).

Figure 8:
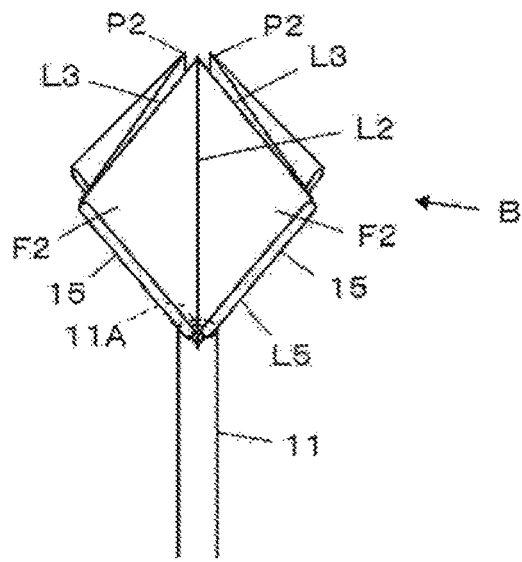
FIG. 8 is a front side perspective view depicting the drug supply device of the embodiment in a state in which the four first folded portions of the drug holding sheet are folded.

Then, as the portions of the straight lines L2 and the straight lines L6 are folded until the portions of the straight lines L2 are positioned on an extension line extending toward the front of the shaft 11 (i.e., an axis line of the shaft 11 in the axial direction extended distally beyond the shaft 11), a second fold body B is formed as depicted in FIG. 8. In the second fold body B, the four second folded portions F2 in which the four first folded portions F1 are folded are disposed around the extension line of the shaft 11

Figure 9:
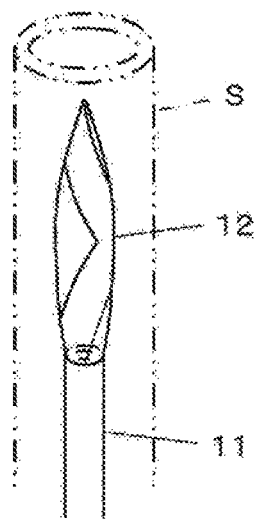
FIG. 9 is a front side perspective view depicting the drug supply device of the embodiment in a state in which the folded drug holding sheet is wrapped around an extension line of the shaft.

Thus, if the four second folded portions F2 are wrapped around the extension line of the shaft 11 after the four balloons 15 are contracted to form the second fold body B from the drug holding sheet 12, then the drug supply device can be passed through a sheath S and inserted into the body of a patient as depicted in FIG. 9.

A hub is attached to the proximal portion of the shaft 11, and such an image diagnosis device such as an IVUS or OCT image diagnosis device can be inserted into the lumen 16 of the shaft 11 through the hub. Further, injection and suction of fluid for development for the four balloons 15 can be performed through the balloon expansion lumen of the shaft 11.

The formation material of the drug holding sheet 12 and the balloons 15 is preferably a material having elasticity and a certain degree of rigidity. For example, the drug holding sheet 12 and/or balloons 15 may be a metal material such as stainless steel, an aluminum alloy, a shape memory alloy, a superelastic alloy or the like and a resin material such as polyamide, polyvinyl chloride, polycarbonate, ABS, polyethylene, polypropylene, polytetrafluoroethylene, cellulose acetate, polyethersulfone, an acrylic resin, a silicon resin or the like can be used.

The shaft 11 material is preferably a material having a certain degree of flexibility, and a metal or a resin can be used. As the metal, for example, a pseudoelastic alloy (including a superelastic alloy) such as a Ni—Ti-based alloy, a shape memory alloy, stainless steel (for example, all kinds of SUS such as SUS304, SUS303, SUS316, SUS316L, SUS316J1, SUS316J1L, SUS405, SUS430, SUS434, SUS444, SUS429, SUS430F, SUS302 and so forth), a cobalt-based alloy, a precious metal such as gold or platinum, a tungsten-based alloy, a carbon-based material (including a piano wire) and so forth can be listed. As a resin, for example, polyolefin (for example, polyethylene, polypropylene, polybutene, ethylene-propylene copolymer, ethylene-vinyl acetate copolymer, ionomer, a mixture of two or more of them and so forth), polymer materials such as polyvinyl chloride, polyamide, polyamide elastomer, polyester, polyester elastomer, polyurethane, polyurethane elastomer, polyimide, fluororesin or the like and mixtures of them, or two or more ones of the aforesaid polymer materials are listed. Also it is possible to configure the shaft 11 from a multilayer tube or the like made of a compound formed from such metals or resins.

Operation of the embodiment of the drug supply device shown in FIGS. 1-9 is next described.

First, the sheath S is inserted into the body of a patient, and the drug supply device in which the drug holding sheet 12 is folded and the four second folded portions F2 are wrapped around an outer periphery of the shaft 11 is inserted into the sheath S (e.g., the drug supply device is inserted into the sheath S before the sheath S is inserted into the body of a patient).

An endoscope or an image diagnosis device (such as an IVUS or OCT image diagnosis device) is inserted in the lumen 16 of the shaft 11 and the environment distal to the distal end of the shaft 11 (i.e., the area beyond the distal end of the shaft 11) is observed. The drug supply device is advanced during this observation until the distal portion of the shaft 11 reaches a position in front of a living body surface such as an outer side surface or an inner side surface of an organ to which drug is to be supplied. Note that, if the drug holding sheet 12 projects from the distal end of the sheath S by advancing the drug supply device relative to the sheath S, then the four second folded portions F2 (having been wrapped around the extension line of the shaft 11) are spaced away from the outer periphery of the shaft 11 until a state depicted in FIG. 8 is established.

The four balloons 15 disposed on the second face 14 of the drug holding sheet 12 are then expanded by injecting development fluid into the balloons 15 through the balloon expansion lumen of the shaft 11, which causes the four second folded portions F2 to gradually expand from the position depicted in FIG. 7 until the first fold body A in which the four first folded portions F1 of a triangular shape are disposed on a plane around the distal end of the shaft 11 is formed as depicted in FIG. 6.

The balloons 15 continue to be expanded, so that the first folded portions F1 are developed (expanded), whereupon the four vertices P1 are progressively spaced away from the distal end of the shaft 11 in the radial direction as depicted in the progression of FIGS. 5 and 4. If the four balloons 15 are expanded fully, then the drug holding sheet 12 is expanded (developed) to establish a state in which the square Q1 substantially perpendicular to the shaft 11 is formed as depicted in FIGS. 1 to 3.

In this state, the drug supply device is advanced (i.e., moved within the living body) until the first face 13 of the developed drug holding sheet 12 is pressed against and brought into contact with the living body surface (i.e., at the treatment site of the human body organ that receives the drug). Consequently, the drug M held on the first face 13 of the drug holding sheet 12 is supplied to the living body surface.

The drug holding sheet 12 is expanded to expose the first face 13 to be moved to contact the living body surface after the drug holding sheet 12 has been carried to the front of the living body surface while the drug holding sheet 12 remains folded such that the first face 13 on which the drug M is held is positioned on the inner side (i.e., the first face 13 is folded inward to protect the drug from being exposed to the living body during the movement of the drug supply device to position the drug holding sheet 12 near the treatment site). Therefore, even if the drug holding sheet 12 is brought into contact with the inner face of the sheath S or with a body organization of the patient while the drug supply device is being maneuvered within the living body, the drug M is prevented from being released from the drug holding sheet 12. This helps allow the drug M to be supplied appropriately to the living body surface. Further, since the drug holding sheet 12 (having been in the folded state) is developed (expanded) to expose the first face 13, supply of the drug M to the living body surface over an overall area can be performed at a time.

After the supply of the drug M to the living body surface is completed, the drug supply device is retracted (i.e., withdrawn from the treatment site) to space the first face 13 of the drug holding sheet 12 away from the living body surface. The development fluid is sucked from within the four balloons 15 through the balloon expansion lumen of the shaft 11 to contract the balloons 15 thereby to form the second fold body B, and then the drug supply device and the sheath S are pulled out from within the body of the patient (i.e., the first face 13 with the drug M is folded inward as described above and shown in the progression of FIGS. 3-9 and then the drug supply device and the sheath S are removed from the living body).

The shaft 11 can be retracted to the sheath S side (i.e., retracted proximally relative to the sheath S) during removal of the drug supply device, so that the drug holding sheet 12 is accommodated in the sheath S and can be pulled out to the outside of the body simultaneously with the sheath S. However, there is no necessity to retract the drug holding sheet 12 into the sheath S during removal of the drug supply device after the drug holding sheet 12 is fully folded until the state of FIG. 8. If the balloons 15 are in a contracted state, then it is possible to retract the drug supply device into the sheath S.

Embodiment 2

In the embodiment described above and illustrated in FIGS. 1-9, if, upon folding of the drug holding sheet 12, the first fold body A depicted in FIG. 6 is formed and then the four balloons 15 are contracted, the four vertices P2 of the first fold body A move to the front of the shaft 11 to form the second fold body B depicted in FIG. 8 when the first folded portions F1 are individually being folded along the straight lines L6. In this second fold body B, the portions on the straight lines L2 are positioned on the extension line directed forwardly of the shaft 11 (i.e., the drug holding sheet 12 protrudes distally beyond the distal end of the shaft 11 as show in FIG. 8).

However, the folding is not limited to the folding method described above. In the embodiment illustrated in FIGS. 10-13, after the first fold body A is formed by beginning to fold the drug holding sheet 12, the drug holding sheet 12 is folded such that, while the first folded portions F1 are being folded on the straight lines L6, the four vertices P2 of the first fold body A are moved toward the proximal side of the shaft 11.

If the four balloons 15 are contracted from a state in which the drug holding sheet 12 is developed to form the square Q1 as depicted in FIG. 3, then the drug holding sheet 12 begins to be folded on the four diagonals L3 similarly as in the embodiment described above regarding FIGS. 1-9. When the drug holding sheet 12 is then folded until the four vertices P1 of the square Q1 upon development (expansion) are overlapped with the distal end of the shaft 11, a first fold body A in which the four first folded portions F1 of a triangular shape are disposed in a plane around the distal end of the shaft 11 is formed (i.e., the first fold body is planar and located at the distal end of the shaft 11).

Figure 10:
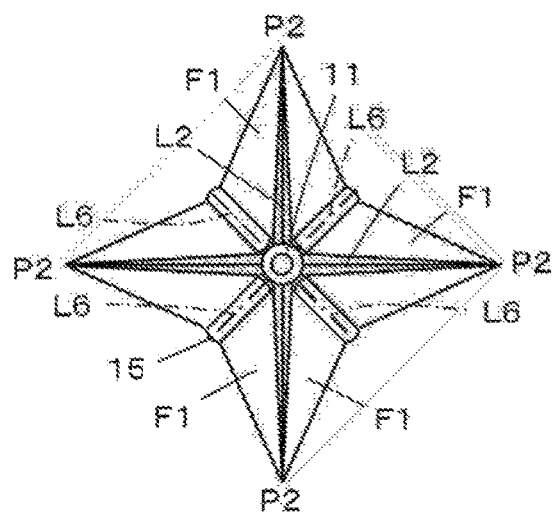
FIG. 10 is a front elevational view of a drug holding sheet as viewed from the front of a shaft, which is in an intermediate state when four second folded portions are folded in another embodiment.

If the four balloons 15 are further contracted from this state, then the drug holding sheet 12 begins to be folded such that portions on the straight lines L2 positioned between adjacent ones of the first folded portions F1 form mountain portions projecting toward the front of the shaft 11 and portions on the straight lines L6 that pass the distal of the shaft 11 having been positioned at the center of the square Q1 and bisect the first folded portions F1 form valley portions that project toward the proximal side of the shaft 11 while the four vertices P2 of the first fold body A of a square shape are positioned on the proximal side of the shaft 11 as depicted in FIG. 10.

Figure 11:
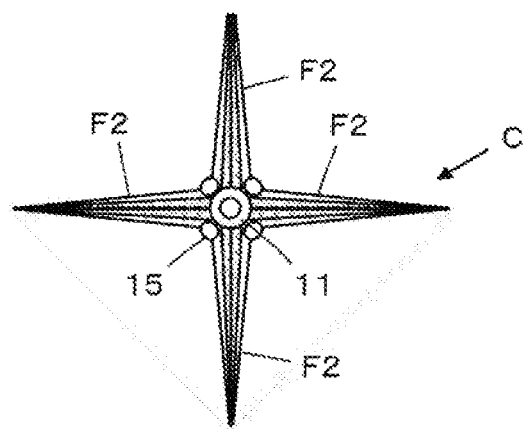
FIG. 11 is a front elevational view of the drug holding sheet as viewed from the front of the shaft, which is in a state in which four first folded portions are folded in the embodiment shown in FIG. 10.
Figure 12:
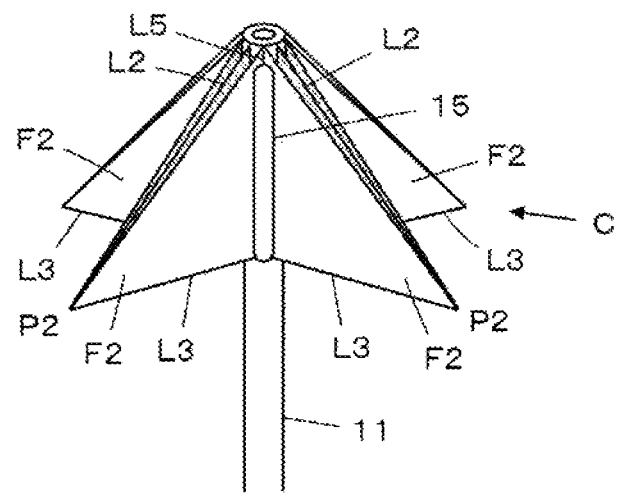
FIG. 12 is a front side perspective view depicting the drug supply device of the embodiment shown in FIG. 10 in a state in which the four first folded portions of the drug holding sheet are folded.

As the portions on the straight lines L2 and the straight lines L6 are then folded until the portions on the straight lines L6 contact the outer periphery of the shaft 11, a second fold body C in which the four second folded portions F2 at which the four first folded portions F1 are folded are disposed around the shaft 11 is formed as depicted in FIGS. 11 and 12.

Figure 13:
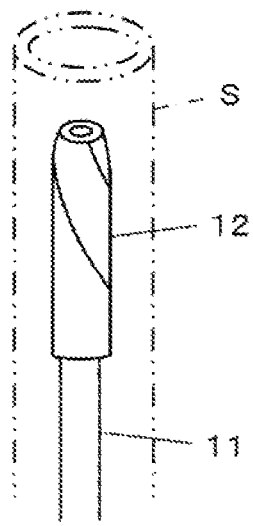
FIG. 13 is a front side perspective view depicting the drug supply device of the embodiment shown in FIG. 10 in a state in which the folded drug holding sheet is wrapped around the shaft.

Therefore, after the four balloons 15 are contracted to form the second fold body C from the drug holding sheet 12, the four second folded portions F2 are wrapped around an outer periphery of the shaft 11 so that the drug supply device can be inserted into the body of a patient through the inside of the sheath S as depicted in FIG. 13.

It is to be noted, however, that there is no necessity to retract the sheath after the developed drug holding sheet 12 is folded fully thereby to form the state of FIG. 12. In some embodiments, the sheath can be retracted if the balloons are in a contracted state.

Even if the drug holding sheet 12 has a fold habit until the drug holding sheet 12 comes to such a second fold body C as described above through the first fold body A, it is possible to supply the drug M appropriately to the living body surface over a great area similarly as in the embodiment 1.

In the embodiments described above in relation to FIGS. 1-13, expansion (unfolding) and contraction (folding) of the drug holding sheet 12 are performed by performing injection and suction of fluid (development fluid) into and from the four balloons 15. It is also possible to dispose, in place of the balloons 15, an expandable member (a development member) made of a shape memory alloy or shape memory polymer or else a resilient material such as polymer or the like on the two diagonals L1 of the second face 14 of the drug holding sheet 12. By inserting the drug holding sheet 12 in a folded state to from a second fold body B into the sheath S and causing the drug holding sheet 12 to project from the distal of the sheath S in the proximity of the living body surface, the expandable member made of a shape memory alloy is expanded and returns to its initial state or the expandable member made of an elastic material is expanded by the elasticity of itself. Then, together with the expansion of the expandable member, the expanded drug holding sheet 12 is developed (formed).

In the embodiments described above regarding FIGS. 1-13, an expandable member formed from the balloons 15 is disposed only on the two diagonals L1 of the square Q1. The positioning of the expandable member is not limited to being only on the two diagonals L1, however, as it is only necessary to structure the development member such that drug application when the expanded drug holding sheet 12 developed to the square Q1 is brought into contact with an affected area (i.e., the target site in the living body) can be performed with (relative) certainty. For example, also it is possible to dispose an expandable member on four sides of the outer periphery of the square Q1. Alternatively, an expandable member may be disposed on the two diagonals L1 and the four sides of the outer periphery of the square Q1 individually. In this last example, the (relative) certainty of expansion of the drug holding sheet 12 can be improved further.

In the embodiments described above and illustrated in FIGS. 1-13, the drug holding sheet 12 has a shape of the square Q1 when expanded. The shape of the drug holding sheet 12, however, is not limited to being a square. The drug holding sheet 12 may have a quadrangular shape other than a square shape or may have a triangular shape or a polygonal shape equal to or greater than a pentagonal shape. The drug holding sheet 12 also may have a shape surrounded by such an outline that includes a curve at least along part of the outer periphery if the drug holding sheet 12 has a plurality of folded portions that can be folded such that the first face 13 on which drug is held may be positioned on the inner side (i.e., so that portions of the first face 13 face one another and towards an interior of the folded shape of the drug holding sheet 12).

The drug M can be directly applied or fixed to the first face 13 of the drug holding sheet 12. It is also possible to dispose the drug M in the form of a patch-shaped therapeutic like a so-called needle patch, a sheet-like drug patch or the like on the first face 13.

Various drugs that are applied in accordance with individual treatments can be used as the drug M.

Embodiment 3

The embodiments described above and shown in FIGS. 1-13 use the balloons 15 as the expandable member. In some embodiments, it is also possible to use balloons 25 having a plurality of bendable nodes 25A as depicted in FIG. 14 in place of the balloons 15.

Figure 14:
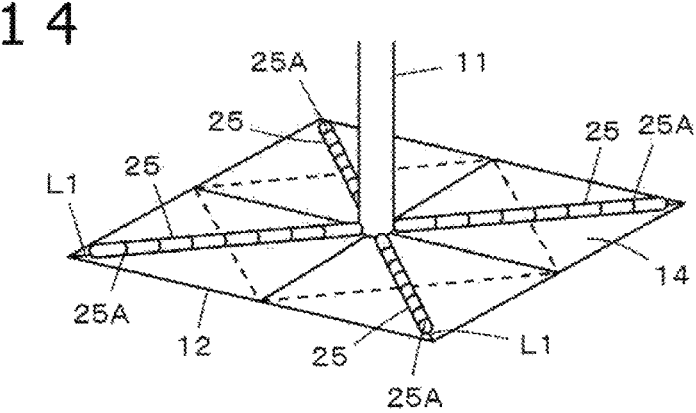
FIG. 14 is a rear side elevational view of a drug supply device according to another embodiment as viewed from the proximal side of a shaft when a drug holding sheet is developed.

The four balloons 25 are configured such that, if development fluid is injected into the balloons 25, the balloons 25 extend substantially perpendicularly to the shaft 11 as depicted in FIG. 14. When the development fluid is suctioned (withdrawn) from the individual balloons 25, then the plurality of nodes 25A are bent such that they are curved at multi stages so as to gradually become concave toward the front of the shaft 11.

Figure 15:
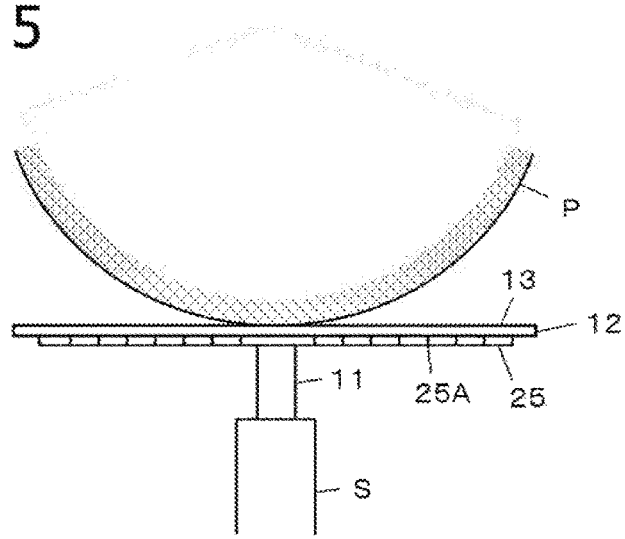
FIG. 15 is a side elevational view depicting the drug supply device according to the embodiment shown in FIG. 14 when the drug holding sheet is developed.
Figure 16:
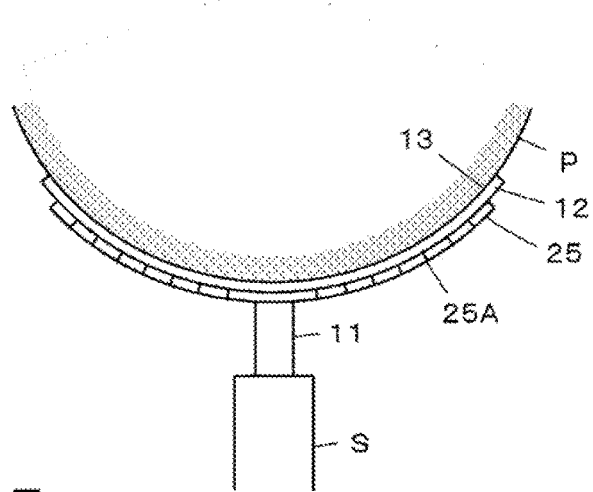
FIG. 16 is a side elevational view depicting the drug supply device according to the embodiment shown in FIG.

Therefore, if the four balloons 25 extend substantially perpendicularly to the shaft 11 as depicted in FIG. 15, the first face 13 of the drug holding sheet 12 is pressed against and brought into contact with a living body surface P that is curved in a convex shape and then the development fluid is gradually sucked from the four balloons 25, the plurality of nodes 25A of the individual balloons 25 are then bent and are curved at multi stages such that they form a concave shape toward the front of the shaft 11. Consequently, as depicted in FIG. 16, the drug holding sheet 12 has a shape following the convex living body surface P and the drug can be supplied while the first face 13 of the drug holding sheet 12 contacts with the living body surface P over a greater range.

Embodiment 4

A needle-shaped member 15A can be individually disposed which projects, when the drug holding sheet 12 is expanded, from the first face 13 toward the front of the shaft 11 as depicted in FIG. 17 at distal portions of four balloons 15 disposed along two diagonals L1 of a square Q1 of a drug holding sheet 12.

The needle-shaped members 15A are configured such that, when the balloons 15 are in a contracted state, the needle-shaped members 15A are positioned along the balloons 15, but when the balloons 15 are expanded, they project, for example, perpendicularly with respect to the first face 13 of the expanded drug holding sheet 12 as depicted in FIG. 17.

A patch-shaped therapeutic 17 is held in front of the drug holding sheet 12 by puncturing the needle-shaped members 15A disposed at the distal portions of the four balloons 15 into the four corners of the patch-shaped therapeutic 17. When the drug holding sheet 12 is expanded, the patch-shaped therapeutic 17 can then be pressed against and brought into contact with the living body surface.

If the needle-shaped member 15A is removably attached to the balloons 15, it is possible to allow the balloons 15 to indwell on the living body surface together with the patch-shaped therapeutic 17 by retracting the balloons 15 and the drug holding sheet 12 after the needle-shaped members 15A puncture an organism of a living body from the living body surface. Consequently, it becomes possible to supply a drug over a long period of time. In order to perform such indwelling of the needle-shaped members 15A, the attachment force of the needle-shaped members 15A to the balloons 15 may be set to a value lower than pulling force required to pull out the needle-shaped members 15A which are punctured in (indwelled in) the organism of the living body.

Similarly, also it is possible to dispose the needle-shaped members 15A at the distal portions of the balloons 25 used in the embodiment shown in FIG. 14.

Embodiment 5

In the embodiments described above and shown in FIGS. 1-13, it is also possible to paste a patch-shaped therapeutic 17 to the first face 13 of the drug holding sheet 12 by a bonding agent 18 as depicted in FIG. 18. The bonding agent 18 has temperature responsiveness and is configured such that, if a predetermined temperature is exceeded, the adhesive strength of the bonding agent 18 decreases. The predetermined temperature can be set, for example, to a value a little lower than the body temperature of the patient.

If the patch-shaped therapeutic 17 is pasted to the first face 13 of the drug holding sheet 12 using such a bonding agent 18 as described above, then after the patch-shaped therapeutic 17 is brought into contact with the living body surface, when the temperature of the bonding agent 18 is increased by the body temperature of the patient until it exceeds the predetermined temperature, the adhesive strength of the bonding agent 18 decreases. Therefore, it is possible to dissect (i.e., remove or peel off) the patch-shaped therapeutic 17 from the first face 13 of the drug holding sheet 12 thereby to allow the patch-shaped therapeutic 17 to be indwelled on the living body surface.

Also it is possible to paste, a patch-shaped therapeutic 17 along the two diagonals L1 of the square Q1 of the drug holding sheet 12 on the first face 13 of the drug holding sheet 12 corresponding to the four balloons 15 in advance using the bonding agent 18 and inject heated development (expansion) fluid into the balloons 15 to raise the temperature of the bonding agent 18 to remove the patch-shaped therapeutic 17 from the first face 13 of the drug holding sheet 12. In this case, the predetermined temperature of the bonding agent 18 can be set to a value higher than the body temperature of the patient, and the patch-shaped therapeutic 17 can be removed from the first face 13 of the drug holding sheet 12 and indwelled on the living body surface without being influenced by the dispersion of the body temperature of individual patients.

Similarly, in the embodiment shown in FIG. 14, the patch-shaped therapeutic 17 may be pasted to the first face 13 of the drug holding sheet 12 by the bonding agent 18.

Embodiment 6

A cross sectional shape of a balloon 35 used in a drug supply device according to another embodiment is depicted in FIG. 19. The balloon 35 has a development fluid injection lumen 35A and a drug supply lumen 35B partitioned from each other by a barrier W.

The development fluid injection lumen 35A is closed at the distal end of the balloon 35. By injecting development fluid into the development fluid injection lumen 35A, the balloon 35 is expanded.

Meanwhile, the drug supply lumen 35B is open at the distal of the balloon 35 and is configured such that a drug supplied through the drug supply lumen 35B can be discharged into the body of the patient from the opening at the distal end of the drug supply lumen 35B.

The opening of the drug supply lumen 35B may be formed in an elongation direction of the drug supply lumen 35B along the balloon 35, or the distal end of the drug supply lumen 35B may extend to a position across an end portion of the drug holding sheet 12 and an opening may be formed at the distal end of the drug supply lumen 35B in a direction orthogonal to the elongation direction of the drug supply lumen 35B so as to be directed to the front of the shaft 11.

A drug discharged from the opening of the drug supply lumen 35B spreads between the drug holding sheet 12 and the living body surface and is supplied over a wide range of the living body surface.

If the drug holding sheet 12 is structured such that drug can be distributed from the second face 14 toward the first face 13, for example, by having a plurality of drug passage holes, then also it is possible for the drug supply lumen 35B to have one or more openings formed intermediately in the elongation direction of the drug supply lumen 35B by being formed from a porous material or the like. The drug discharged from such an opening or openings circulates from the second face 14 side to the first face 13 side of the drug holding sheet 12 and spreads between the first face 13 and the living body surface.

Furthermore, the distal portion of the shaft 11 may be configured such that it is exposed to a central portion of the first face 13 of the drug holding sheet 12 as depicted in FIG. 1 and drug is discharged between the drug holding sheet 12 and the living body surface from the distal portion of the shaft 11 through a balloon expansion lumen formed on a wall portion of the shaft 11.

In the embodiment described above and shown in FIG. 19, the development fluid injection lumen 35A and the drug supply lumen 35B are disposed in parallel to each other in the inside of the same balloon 35. It is also possible, however, to form a balloon, in which a development fluid injection lumen is formed, and a tube, in which a drug supply lumen is formed, independently of each other.

The detailed description above describes a drug supply device and drug supply method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A drug supply device to be introduced into a living body for supplying a drug to a living body surface in the living body, comprising:
    an elongated shaft extending in an axial direction, the elongated shaft possessing a proximal end and a distal end portion;
    a drug holding sheet attached to the distal end portion of the shaft and having a first face and a second face opposite the first face;
    a drug applied on the first face of the drug holding sheet;
    an expandable member disposed on the second face of the drug holding sheet, the expandable member being expandable and contractible, expansion of the expandable member causing the drug holding sheet to expand from a folded state into an expanded state;
    the first face of the drug holding sheet facing distally when the drug holding sheet is in the expanded state and the second face facing proximally when the drug holding sheet is in the expanded state, the drug holding sheet including a plurality of folded portions configured to fold such that the first face is positioned to face radially inwardly so that parts of the first face directly face one another when the drug holding sheet is in the folded state; and
    the drug supply device being configured to be positioned in the living body so that the first surface of the drug holding sheet contacts a living body surface while the expandable member is in the expanded state to supply the drug on the first surface of the drug holding sheet to the living body surface and to be removed from the living body after contacting the living body surface with the first surface of the drug holding sheet and after supplying the drug on the first face of the drug holding sheet to the living body surface.

2. The drug supply device according to claim 1, wherein the drug holding sheet forms a quadrangle when the drug holding sheet is expanded into the expanded state.

3. The drug supply device according to claim 2, wherein a center of the quadrangle is attached to a distal end of the shaft,
    the plurality of folded portions include four first folded portions of a triangular shape folded such that four corners of the drug holding sheet overlap with the center of the quadrangle and four second folded portions folded such that straight line portions positioned between adjacent ones of the first folded portions form mountain portions that project distally beyond the shaft and straight line portions that pass the center of the quadrangle and bisect the individual first folded portions form valley portions that project toward the proximal end of the shaft relative to the mountain portions, and the expandable member is disposed along two diagonals of the quadrangle.

4. The drug supply device according to claim 3, wherein, during the drug holding sheet expansion by the expandable member, the four second folded portions are individually developed and then the four first folded portions are individually developed after the four second folded portion have been developed.

5. The drug supply device according to claim 3, wherein the first face extends substantially perpendicularly to the shaft when the drug holding sheet is expanded into the expanded state.

6. The drug supply device according to claim 3, comprising a needle-shaped member which projects distally beyond the distal end of the shaft when the drug holding sheet is expanded to the expanded state.

7. The drug supply device according to claim 6, further comprising:
a patch-shaped therapeutic attached to the needle-shaped member.

8. The drug supply device according to claim 7, wherein the needle-shaped member is removably disposed on the expandable member and is configured to be indwelled on living body surface together with the patch-shaped therapeutic when the drug supply device supplies the drug on the first face of the drug holding sheet to the living body surface.

9. The drug supply device according to claim 2, wherein the expandable member is configured from a shape memory member.

10. The drug supply device according to claim 2, further comprising:
a patch-shaped therapeutic adhered to the first face of the drug holding sheet by a temperature-response bonding agent, wherein,
when a predetermined temperature is exceeded, the patch-shaped therapeutic is removed from the first face of the drug holding sheet and is configured to be indwelled on the living body surface.

11. The drug supply device according to claim 2, wherein the expandable member is disposed along the two diagonals of the quadrangle comprises a drug supply lumen through which the drug is supplied, the drug supplied through the drug supply lumen being discharged from a distal portion of the expandable member.

12. The drug supply device according to claim 1, wherein the expandable member is a plurality of balloons which are each expandable by injecting fluid into the respective balloon and contractible by removing the fluid from the balloon.

13. The drug supply device according to claim 12, wherein
each of the plurality of balloons comprises a plurality of bendable nodes,
when the fluid is injected into each of the plurality of balloons, the plurality of balloons extend substantially perpendicularly to the shaft, and
when the fluid is removed from each of the plurality of balloons, the balloons are gradually curved at multiple stages so as to become concave toward the distal end portion of the shaft.

14. The drug supply device according to claim 1, wherein the shaft comprises a lumen formed along the axial direction of the shaft.

15. A drug supply device for supplying a drug to a surface of a treatment site within a living body, the drug supply device comprising:

an elongated shaft extending in an axial direction, the elongated shaft possessing a distal end portion and a proximal end;
a drug holding sheet attached to the distal end portion of the shaft, the drug holding sheet comprising a first surface and a second surface opposite the first surface, the first surface of the drug holding sheet being coated with a drug;
the drug holding sheet comprising a fold pattern of fold lines that causes the drug holding sheet to be planar when the drug holding sheet is fully unfolded in an unfolded state and causes the drug holding sheet to be folded when the drug holding sheet is fully folded into a folded state, the drug holding sheet having an interior when folded into the folded state;
an expandable member connected to the second surface of the drug holding sheet, the expandable member being expandable to expand the drug holding sheet from the folded state into the unfolded state;
the first surface of the drug holding sheet facing distally from the distal end portion of the elongated shaft when the drug holding sheet is in the unfolded state and the second surface of the drug holding sheet facing proximally towards the proximal end of the elongated shaft when the drug holding sheet is in the unfolded state;
the first surface of the drug holding sheet facing inward when the drug holding sheet is in the folded state and the second surface of the drug holding sheet facing outward when the drug holding sheet is in the folded state such that the second surface directly faces an environment beyond the drug supply device while portions of the first surface face one another by facing towards the interior; and
the drug supply device being configured to be positioned in the living body so that the first surface of the drug holding sheet contacts a living body surface while the expandable member is in the unfolded state to supply the drug on the first surface of the drug holding sheet to the surface of the treatment site in the living body and to be removed from the living body after contacting the living body surface with the first surface of the drug holding sheet and after supplying the drug on the first surface of the drug holding sheet to the living body surface.

16. The drug supply device according to claim 15, wherein
the elongated shaft possesses a longitudinal axis in the axial direction, and
the plane of the drug holding sheet in the unfolded state is perpendicular to the longitudinal axis of the elongated shaft.

17. The drug supply device according to claim 15, wherein
the drug holding sheet extends further in a distal direction relative to the shaft when the drug holding sheet is in the folded state compared to when the drug holding sheet is in the unfolded state.

18. A drug supply device to be introduced into a living body for supplying a drug to a living body surface in the living body, comprising:
an elongated shaft extending in an axial direction, the elongated shaft possessing a proximal end and a distal end portion;
a drug holding sheet attached to the distal end portion of the shaft, the drug holding sheet possessing first and second faces that face in opposite directions;
a drug on the first face of the drug holding sheet;

at least one balloon mounted on the second face of the drug holding sheet, the at least one balloon being expandable upon introducing fluid into the at least one balloon to expand the drug holding sheet into an expanded state, the at least one balloon being contractible upon discharging the fluid from the at least one balloon to change the drug holding sheet to a folded state;

the first face of the drug holding sheet facing distally when the drug holding sheet is in the expanded state and the second face of the drug holding sheet facing proximally when the drug holding sheet is in the expanded state, the drug holding sheet including a plurality of folded portions that face inwardly when the drug holding sheet is in the folded state so that portions of the first face are arranged to face one another; and the drug supply device being configured to be positioned in the living body so that the first face of the drug holding sheet contacts the living body surface while the at least one balloon is in the expanded state to supply the drug on the first face of the drug holding sheet to the living body surface and to be removed from the living body after contacting the living body surface with the first face of the drug holding sheet and after supplying the drug on the first face of the drug holding sheet to the living body surface.

19. The drug supply device according to claim 18, wherein the at least one balloon mounted on the second face of the drug holding sheet includes a plurality of balloons mounted on the second face of the drug holding sheet, the plurality of balloons being circumferentially spaced apart from one another on the second face of the drug holding sheet, each of the plurality of balloons projecting radially outwardly away from a central axis of the elongated shaft when the drug holding sheet is in the expanded state.

20. The drug supply device according to claim 18, wherein the drug is part of a patch-shaped therapeutic that face inwardly when the drug holding sheet is in the folded state so that portions of the first face are arranged to face one another.

* * * * *